United States Patent
Fu et al.

(10) Patent No.: US 11,761,954 B2
(45) Date of Patent: Sep. 19, 2023

(54) NBOME TEST

(71) Applicant: University of Technology Sydney, Ultimo (AU)

(72) Inventors: Shanlin Fu, Ultimo (AU); Laura Jane Clancy, Ultimo (AU); Morgan Philp, Ultimo (AU); Ronald Shimmon, Ultimo (AU)

(73) Assignee: University of Technology Sydney

( * ) Notice: Subject to any disclaimer, the term of this patent is extended or adjusted under 35 U.S.C. 154(b) by 393 days.

(21) Appl. No.: 17/269,417

(22) PCT Filed: Aug. 22, 2019

(86) PCT No.: PCT/AU2019/050888
§ 371 (c)(1),
(2) Date: Feb. 18, 2021

(87) PCT Pub. No.: WO2020/037372
PCT Pub. Date: Feb. 27, 2020

(65) Prior Publication Data
US 2021/0190766 A1    Jun. 24, 2021

(30) Foreign Application Priority Data
Aug. 22, 2018   (AU) ................................ 2018903082

(51) Int. Cl.
*G01N 33/52*   (2006.01)
*G01N 21/78*   (2006.01)

(52) U.S. Cl.
CPC ........... *G01N 33/523* (2013.01); *G01N 21/78* (2013.01)

(58) Field of Classification Search
CPC ...... G01N 33/523; G01N 21/78; G01N 31/22; C07C 221/00; C07C 39/08; C07C 49/675; C07C 50/24; C07C 255/33; C07D 217/22
See application file for complete search history.

(56) References Cited

PUBLICATIONS

Syam, B. M. et al., "Development of new visible spectrophotometric methods for quantitative determination of almotriptan malate using quinones as chromogenic reagents", Chemical Science Transactions (2012), 1(2), pp. 297-302. see Method M2 p. 300, and Figure 6.

Kumble, D. et al., "New visible spectrophotometric methods for the determination of protriptyline HCl in bulk and pharmaceutical formulations", Journal of Chemical and Pharmaceutical Research (2012), 4(9), pp. 4352-4358 see Method A p. 4353-4354 and scheme 1.

Kalyanaramu, B. et al., "Development of new visible spectrophotometric assay for ramipril estimation in bulk and formulations using quinone as chromogenic reagent", International Journal of ChemTech Research (2011), 3(3), pp. 1279-1284 see Materials and methods pp. 1280 and Fig. 4.

(Continued)

*Primary Examiner* — Jennifer Wecker
*Assistant Examiner* — Ali Husain Faraz
(74) *Attorney, Agent, or Firm* — The Belles Group, P.C.

(57) ABSTRACT

A method of detecting the presence of an NBOMe in a sample which comprises of contacting the sample with an activated p-quinone such as 2,3,5,6-tetrachloro-1,4-benzoquinone (TCBQ) and an aldehyde, for example acetaldehyde, and optionally a buffer and observing a colour change, which when present, correlates with the presence of an NBOMe. The ingredients may be provided in the form of a kit which can include a colour standard or comparison chart.

20 Claims, 4 Drawing Sheets

(56) References Cited

PUBLICATIONS

Attia, F. M., "Use of charge-transfer complex formation for the spectrophotometric determination of nortriptyline", Il Farmaco (2000), 55(11-12), pp. 659-664 see Method C p. 660.

Dean, B. V. et al., "2C or Not 2C: Phenethylamine Designer Drug Review", Journal of Medical Toxicology, 2013, 9(2), pp. 172-178 see whole document.

Stellpflug, S. J. et al., "2-(4-Iodo-2,5-dimethoxyphenyl)-N-[(2-methoxyphenyl)methyl]ethanamine (25I-NBOMe): Clinical Case with Unique Confirmatory Testing", Journal of Medical Toxicology, 2014, 10(1), pp. 45-50 see whole document.

Oiye, E. N. et al., "Electrochemical analysis of 25H-NBOMe by Square Wave Voltammetry", Forensic Chemistry (2017), 5, pp. 86-90 see whole document.

Botch-Jones, S. et al., "The detection of NBOMe designer drugs on blotter paper by high resolution time-of-flight mass spectrometry (TOFMS) with and without chromatography", Forensic Science International (2016), 267, pp. 89-95 see whole document.

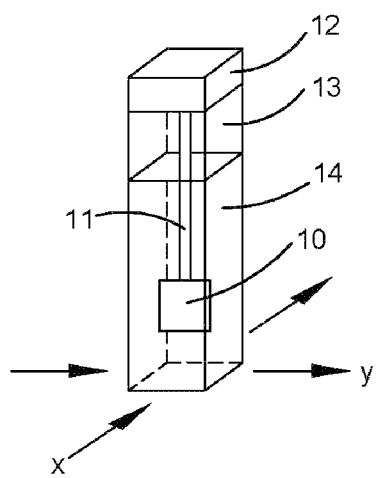
FIG. 1a
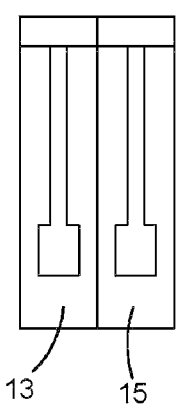
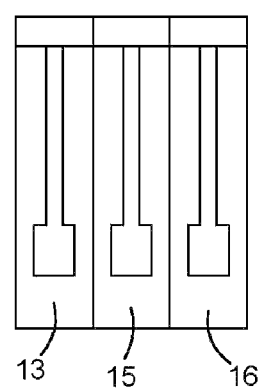
FIG. 1b          FIG. 1c

NBOME TEST

CROSS-REFERENCE TO RELATED PATENT APPLICATIONS

The present application is a U.S. national stage application under 35 U.S.C. § 371 of PCT Application No. PCT/AU2019/050888, filed Aug. 22, 2019, which claims priority to Australian Patent Application No. 2018903082, filed Aug. 22, 2018. The disclosures of the aforementioned priority applications are incorporated herein by reference in their entireties.

FIELD OF THE INVENTION

The invention relates to tests for the determination of illicit substances. In particular, the invention relates to tests for the detection of drugs of the NBOMe family. The invention also relates to kits and devices for the detection of NBOMes.

BACKGROUND

The present-day illicit drug trade is a large, lucrative, global industry. Technological advances and the ingenuity of rogue chemists continues to present ongoing challenges for law enforcement authorities and for scientists and engineers developing the technology to support them.

In recent years, the recreational drug market has seen an increase in the abuse of New Psychoactive Substances (NPS). NPS exhibit psychotropic effects when taken and are often an alternative to traditional illicit drugs. NPS are often derivatives or analogues of existing illicit drugs, pharmaceutical compounds, substances being researched or naturally occurring compounds. Studies in recent years have provided an understanding for the motivations to use NPS. These include potentially ambiguous legal status (motivated by a desire to avoid detection), market availability and cost. NPS may also function as market substitutes for established illicit drugs during times when these are of limited availability or poor quality.

NPS are of great concern due to the number and diversity of compounds involved and a lack of knowledge about their mode of action, side effects and toxicity, although it is clearly established that many NPS have been linked to adverse neurological and psychological outcomes.

NBOMes are some of the most recent NPS to appear on the market, although these substances are only "new" in the sense of being newly misused, as nearly all were synthesized many years ago. NBOMe compounds are a class of methoxy benzyl substituted phenethylamine compounds which provide hallucinogenic and psychoactive properties at extremely low dosages—as little as 200 µg when taken intranasally or sublingually and even less if smoked as the free base. They raise serious health risks for users, particularly in relation to hypertension and tachycardia and a number of deaths have been reported. The high potency of these drugs means that overdoses are common.

NBOMes are illegal or controlled by legislation in most jurisdictions, although they are often sold as "legal LSD". They are commonly sold in the form of blotter papers or powders.

NBOMes are a well-defined class of NPS and their structure typically includes a base 2,5-dimethoxy-phenethylamine or "2C" structure, which itself may have psychoactive properties, as well as a 2-methoxybenzyl group on the 2C nitrogen. The structure below shows a 2,5-dimethoxy-N-(2-methoxybenzyl)phenethylamine (25-NBOMe) structure with a variable 'R' substituent at position 4. The addition of the 2-methoxybenzyl substituent is highly significant in altering the chemical and pharmacological properties of the resultant NBOMe, which has been shown to produce a 190-fold affinity for the 5-HT2A receptors compared to the unsubstituted compound.

The most common NBOMes are shown below:

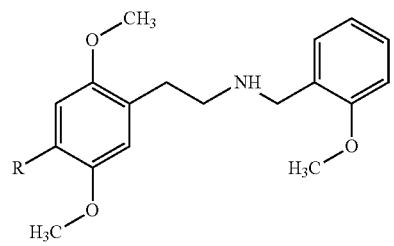

| Compound | Position 4 'R' substituent |
| --- | --- |
| 25B-NBOMe | Bromine |
| 25C-NBOMe | Chlorine |
| 25D-NBOMe | Methyl |
| 25E-NBOMe | Ethyl |
| 25F-NBOMe | Fluorine |
| 25G-NBOMe | Dimethyl (3 and 4 positions) |
| 25H-NBOMe | Hydrogen |
| 25I-NBOMe | Iodine |
| 25N-NBOMe | Ethylthio |
| 25P-NBOMe | Propyl |
| 25TFM-NBOMe | Trifluoromethyl |

In order to prosecute those involved with illegal drugs, it is necessary to be able to identify the drugs present. NBOMes can be identified by traditional analytical techniques such as Gas Chromatography-Mass Spectrometry (GC-MS) and High-Performance Liquid Chromatography-Mass Spectrometry (HPLC-MS). The analysis of NBOMe's can be particularly challenging as it may require extraction (from blotters) and possibly derivatisation before analysis. Mass spectrometry can be can be complicated as the close structural similarity of the compounds means that NBOMes often give similar base peaks and fragmentation patterns. Importantly, there is a lack of library data to enable direct comparison.

Other analytical methods, such as NMR are highly reliable for the structural determination of NBOMe's, although these are not ideal for high throughput sample analysis owing to their high cost of running, the need for trained personnel and lengthy analysis times.

The large number of illicit drug seizures means that simple, rapid, inexpensive, and accurate field tests are highly desirable.

Presumptive screening tests are designed to provide an indication of the presence or absence of certain drug classes in a test sample. They need to be simple to carry out, robust enough to be used under sub-optimal conditions and sufficiently reliable so they can form the basis for the legal detention of suspects until definitive tests can be completed.

Colour 'spot' tests are a particularly useful type of field test that result in a colour change when applied to a sample containing a drug of interest. The chemical reaction occurring between the colour reagent and the drug of interest provides a very rapid first line screening tool which can, in some cases, be quite selective.

There is currently no commercially available presumptive colour test for NBOMe's. Attempts to use colour tests to detect NBOMe's as described in the literature have yielded mixed results.

A study completed by Cuypers et al. [Drug Testing and Analysis, 2015] on the colour testing of a number of NPS showed that NBOMe compounds along with other NPS appear to give a colour change or positive result to some well-known and commonly used colour tests. NBOMe compounds were found to react with Scott's reagent (cobalt thiocyanate test) which gives a blue colour with cocaine. Most, but not all NBOMe compounds, gave a greenish colour which would could be wrongly interpreted as a positive result for cocaine. These results are not suitable for use in casework.

Tests originally created for other traditional illicit drugs have been tried and tested with NBOMe compounds. For example, the Marquis reagent is one of the most common tests used for identifying a range of illicit drugs and has been used by some to test NBOMe compounds. This does result in a colour change when applied, but different NBOMe compounds react slightly differently to this reagent and give a different colour result. Also, it appears from the literature that the application of the same test has resulted in different colour changes for the same compound indicating that the test is not reliable for these compounds.

NBOMe substances also do not give a reliable positive result on rapid drug immunoassays [Stellpflug, S. J., et al., Journal of Medical Toxicology, 2014.].

Thus, there is a clear need for a new specific colour test for the presumptive testing of NBOMes.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY

According to a first aspect the invention provides a method of detecting the presence of an NBOMe in a sample, the method comprising the steps of contacting the sample with an activated para-quinone, and an aldehyde and observing a colour change, which when present, correlates with the presence of an NBOMe.

An activated para-quinone is for preference once which is substituted with one or more good leaving groups, such as a halide or a sulfonate. Halides are preferred substituents, with Cl and Br being particularly preferred.

Preferably the active para-quinone is a symmetrical quinone, i.e. possessing at least one point, line or plane of symmetry. Thus, di or tetra substituted para-quinones are preferred. One particularly preferred quinone is 2,3,5,6-tetrachloro-1,4-benzoquinone (TCBQ). Other examples of symmetrical quinones include 2,3,5,6-tetrabromo-1,4-benzoquinone, 2,3-dibromo-1,4-benzoquinone, 2,3-dichloro-1,4-benzoquinone, 2,6-dibromo-1,4-benzoquinone or 2,6-dichloro-1,4-benzoquinone.

In alternative embodiments the quinones may be, for example, 2,5-dibromo or 2,5-dichloro-1,4-benzoquinone.

Preferably, the aldehyde is acetaldehyde.

The activated para-quinone may be provided in a suitable solvent, for instance, a solvent such as ethyl acetate, methanol or 1,4-dioxane.

A buffer is preferably added to maintain an alkaline environment, most preferably in the range pH 7.6 to 12 For preference the buffer is a phosphate buffer, such as a buffer solution which comprises $NaH_2PO_4$—NaOH buffer of pH 11.4 Preferably, the aldehyde and the active p-quinone are present in equimolar amounts. For instance, the acetaldehyde and TCBQ may be present in an amount of $1\times10^{-3}M$ to $1\times10^{-2}M$, such as $3\times10^{-3}M$ The colour change is observed at environmental temperature within 5 minutes.

In one embodiment, the order of addition to the sample is:
1) buffer
2) a solution of TCBQ and acetaldehyde.

Alternatively, the buffer, TCBQ and acetaldehyde are contacted simultaneously with the sample. In a further alternative, the acetaldehyde is contacted with the sample prior to the addition of TCBQ.

Preferably, the method takes place on a plate or well to allow visualisation of developed colour, where present, or in a vessel having a reduced or tapering cross section at a lower portion of the vessel.

The sample may be an unknown drug sample and the method is used as a presumptive test for a suspected illicit substance or as a presumptive test for a suspected overdose or as a presumptive test in sport or workplace testing.

According to a second aspect, the invention provides a test reagent for detecting the presence of an NBOMe in a sample, the reagent comprising TCBQ and acetaldehyde and a solvent The test reagent may further comprise a solvent selected from 1,4-dioxane and ethyl acetate.

The test reagent may further comprise a buffer, such as a phosphate buffer.

According to a third aspect the invention provides a kit for the detection of an NBOMe cathinone moiety, the kit comprising the test reagent of the second aspect. The kit may also further comprise a colour standard or comparison chart.

In another aspect, the invention provides the following NBOMe adducts:

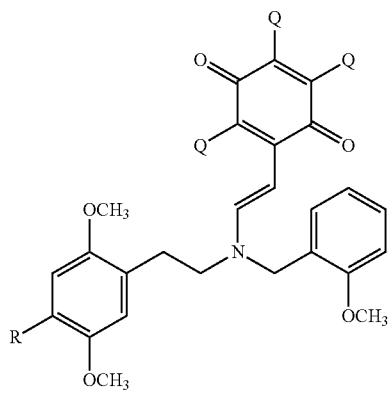

Where R=H, F, Cl, Br, I, Methyl, Ethyl, Propyl, Butyl, S-Ethyl, $CF_3$ and Q is independently selected from H, Cl or Br, or

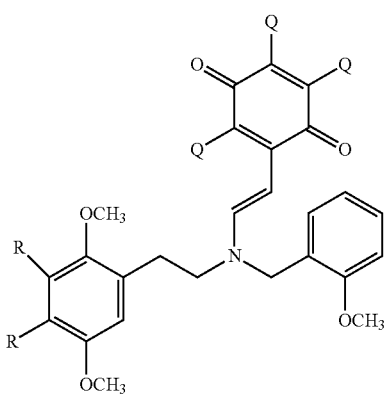

Where R is independently selected from H, F, Cl, Br, I, Methyl, Ethyl, Propyl, Butyl, S-Ethyl, CF$_3$ and Q is independently selected from H, Cl or Br.

BRIEF DESCRIPTION OF THE DRAWINGS

FIGS. 1a-c shows devices suitable for the detection of the colour change.

DESCRIPTION

Figure 2:
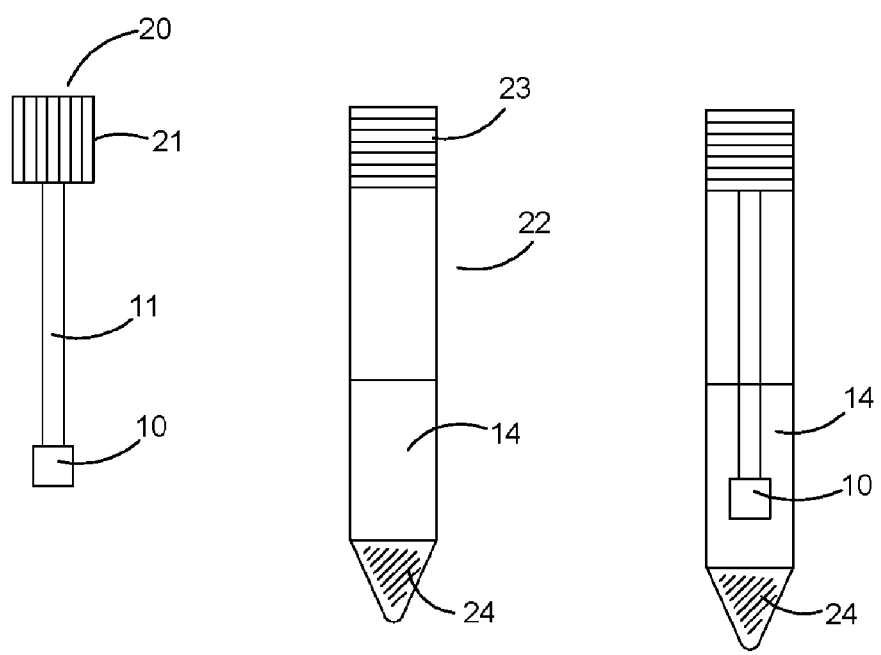
FIG. 2 shows kits or devices suitable for the detection of the colour change.

As outlined above there is currently no presumptive colour test that will correctly identify 25-NBOMe compounds selectively from other illicit compounds.

The amine functional group would be a potential candidate as a reactive centre. However, an amine functional group is not unique to NBOMes and there are many other illicit compounds (such as phenethylamines) containing an amine group with similar base structures. 2,3,5,6-tetrachloro-1,4-benzoquinone (TCBQ) has previously shown to produce coloured products upon reaction with amines. A study conducted by Walash et al. [*Int J Biomed Sci*, 2010] on the determination of phenylpropanolamine (PPA) using a spectrophotometric method showed that TCBQ can produce a coloured product with this particular compound. The present inventors tested TCBQ against several 2C—H (phenylethylamine) analogues and observed a yellow-green colour change in some cases, however the overall results were variable and non-specific, rendering the TCBQ test unsuitable as a presumptive test for 2C compounds.

Surprisingly, the present inventors have found that an activated p-quinone such as TCBQ forms a distinct blue coloured adduct with NBOMes in the presence of an aldehyde such as acetaldehyde with high specificity, selectivity and sensitivity, making it an ideal presumptive test for NBOMes.

Without wishing to be bound by theory, it is believed that the addition the adduct of NBOMe, aldehyde and activated p-quinone forms a compound in which the electronic structure is perturbed in such a way to provide a distinctive blue colour.

The general mechanism of the reaction is shown below as illustrated with 25H NBOMe, TCBQ and acetaldehyde. The reaction takes place in a suitable organic solvent is required.

The secondary amine first forms an adduct with the aldehyde which in turn reacts with the TCBQ.

A buffer is ideally present to ensure the 25H-NBOMe is in free base form for reacting with the aldehydes. Also, the second step of the reaction scheme involves the elimination of HCl, so it is helpful to have a buffer present to ensure the coloured TCBQ adduct likewise remains in free base form, rather than as a salt to ensure that it remains dissolved in the solution and able to provide a solution which can be adequately visualised.

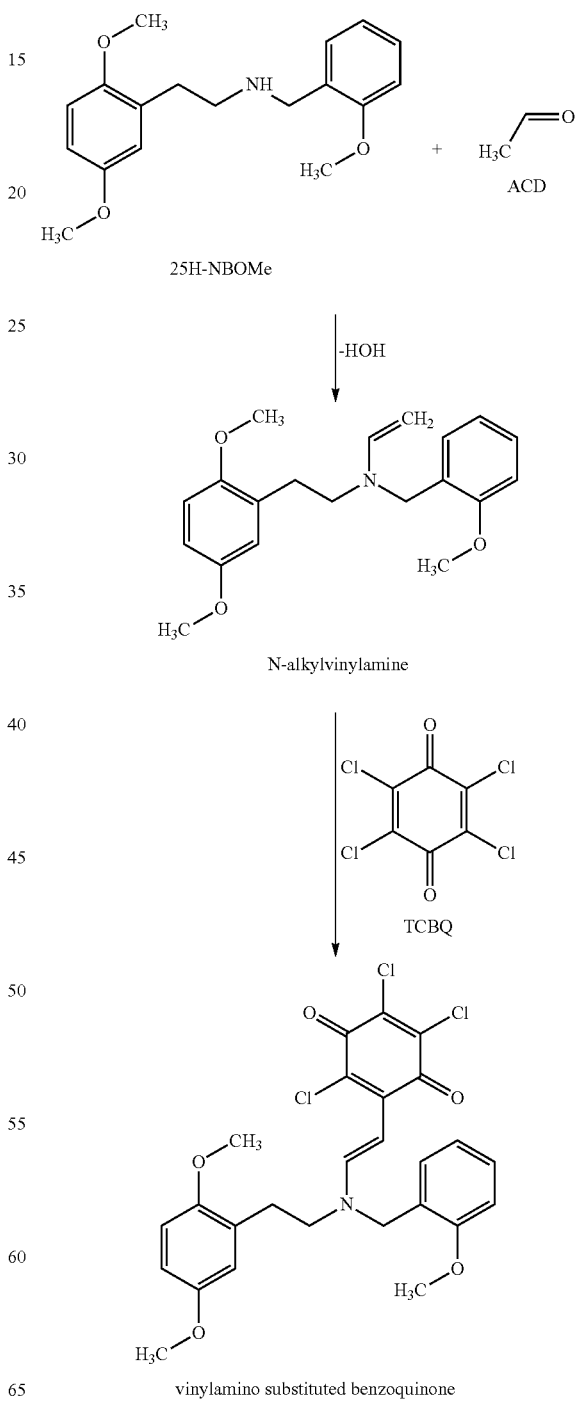

The resultant NBOMe/aldehyde/TCBQ ternary adduct, which can be characterised as a vinylamino substituted benzoquinone, has an intense blue colour.

A very important requirement for a presumptive test is reliability. It is important that the test does not have too many false negatives (in this case, testing negative for a significant number of NBOMe derivatives), or too many false positives (leading to the detention of too many suspects that will ultimately not lead to convictions).

The invention is illustrated here with reference to TCBQ, although it is envisaged that the reaction may proceed in a similar manner with related substituted quinones of similar reactivity.

The present inventors have shown that the nature of the substituents and the symmetry of the quinone are important factors driving the ability of such activated quinones to form ternary adducts with an aldehyde and an NBOMe with sufficient specificity and clarity to be useful as a presumptive test.

The testing of a number of ortho- and para-substituted benzoquinones established that a para-substituted benzoquinone (a 1,4-benzoquinone) was required. Ortho-quinones tested, such as o-TCBQ showed a different colour change with 25H-NBOMe (orange rather than blue) compared to the para-counterpart and there was also less differentiation between the tested sample and the blank.

The quinones that were found to be most useful in presumptive testing contained one or more good leaving groups, such as a halogen, in particular chlorine or bromine. This is believed to be important for reaction with the intermediate vinylamine.

It was found to be important that the quinone had a plane of symmetry. In the cases where trichloro-para-benzoquinone was used, no colour suitable for a presumptive test was observed. Di- or tetra-substituted para-benzoquinones appeared to give the clearest and most consistent results. Suitable quinones include 2,3,5,6-tetrachloro-1,4-benzoquinone, 2,3-dibromo-1,4-benzoquinone, 2,3-dichloro-1,4-benzoquinone, 1,6-dibromo-1,4-benzoquinone or 1,6-dichloro-1,4-benzoquinone.

Tested compounds not possessing the p-benzoquinone skeleton, leaving group and symmetry requirements included hydroquinone, benzoquinone, 2,3-dicyanohydroquinone, 2,3-dichloro-5,6-dicyano-1,4-benzoquinone (DDQ), 2-hydroxy-1,4-naphthoquinone and quinhydrone. These were tested against a range of illicit substances including NBOMes, under various conditions. Whilst several of the quinone derivatives were seen to form coloured compounds with the 25H-NBOMe, many showed similar colour changes with other secondary amines. None of the alternative quinones exhibited anything like the required selectivity and sensitivity of the symmetrical activated para-quinones such as TCBQ. DDQ was able to give coloured compounds in the presence of NBOMe's, but these were observed with and without the aldehyde present and moreover were not specific for NBOMe's but were observed for a variety of secondary amines. Without wishing to be bound by theory, it is thought that such DDQ was forming charge transfer complexes directly with the NBOMe.

The nature of the aldehyde used in the presumptive test is also important. Using acetaldehyde gave the bright blue colour change indicative of NBOMe's. However, the use of longer chain aldehydes failed to give intense or consistent colour changes under similar conditions (e.g. pale green, pale orange)

The method of the present invention will be described herein with reference to 2,3,5,6-tetrachloro-1,4-benzoquinone, which is a readily available quinone, but it will be appreciated that it is applicable to the other activated symmetrical para-quinones described above.

The test process itself is relatively simple:

A small amount of suspected illicit sample (around pin head size) is treated with a small quantity (few drops) of buffer to ensure that any NBOMe form is present in the free base form.

The buffered solution is then treated with a solution of the quinone (such as TCBQ) in a suitable organic solvent (few drops).

The mixture is then treated with acetaldehyde (few drops) and the colour is observed. After 3-5 minutes, the colour is observed again.

The presence of a blue colour after 3-5 minutes, which can be compared with a reference sample, provides a positive presumptive test for the presence of an NBOMe.

The limits of the reaction were explored by comparative testing against a known NBOMe, 25H-NBOMe. Variables included the solvent, the aldehyde, the buffer, the quantities of the reagents and the order of addition.

Any solvent used is required to have good solvency for quinones such as TCBQ, be inert to the other agents present and ideally non-hazardous for human health.

1,4-Dioxane was tested and found to be a suitable solvent. Ultimately, it was found that ethyl acetate gave excellent results in terms of the brightness of the colour change and the range of solubility, but without the accompanying toxicity issues.

Methanol gave acceptable results but other alcoholic solvents, such as ethanol, propanol, butanol are less preferred. and are generally poorer solvents for quinones. Other solvents such as chloroform, THF and acetone gave less intense and less reliable colour changes. The following table illustrates the basis for solvent selection:

| Solvent | Solubility | Colour change | Potential hazards |
|---|---|---|---|
| Ethyl acetate | Soluble | Bright blue | Flammable, harmful |
| 1,4-dioxane | Soluble | Blue | Flammable, harmful, health hazard |
| Methanol | Just soluble | Light blue | Flammable, toxic, health hazard |
| Ethanol | Sparingly soluble | v. pale brown | Flammable, harmful, health hazard |
| Propanol | Sparingly soluble | v. pale brown | Flammable, harmful |
| Diethyl ether | Sparingly soluble | Light brown-green | Flammable, harmful |
| THF | Soluble | Dark purple | Flammable, harmful, health hazard |
| Chloroform | Soluble | Blue-green | Toxic, harmful, health hazard |
| Acetone | Soluble | Green | Flammable, harmful |
| Water | Insoluble | — | None |

Aldehydes having at least 2 carbons and an α-H may theoretically participate in the reaction, however, any aldehyde having a substituent other than hydrogen on the α carbon would serve no purpose and may result in adverse steric consequences for the final adduct. In practical terms, acetaldehyde is the aldehyde of choice for the test.

The reaction was found to be relatively insensitive to the quantity or means of addition of acetaldehyde.

For instance, the acetaldehyde could be added in relatively dilute form, as an 8% solution, however, the reaction proceeded most cleanly when neat acetaldehyde was added.

The following tables show how the colour change varied as a function of quinone, and aldehyde against 2CH and 25H-NBOMe:

|  | Acetaldehyde | | |
|---|---|---|---|
| Reagent | Blank | 2CH | 25H-NBOMe |
| 2,3,5,6-tetrachloro-1,4-benzoquinone (p-TCBQ) | colourless | green | bright blue |
| 3,4,5,6-tetrachloro-1,2-benzoquinone (o-TCBQ) | yellow | bright red | pale orange |
| 2,5-Dichloro-1,4-benzoquinone | v. pale pink | pale blue | dark blue |
| 2,6-Dichloro-1,4,-benzoquinone | v. pale yellow-pink | light blue | bright blue |
| Chloranilic acid | light pink-purple | light pink-purple | light yellow-pink |
| 2,3,5,6-tetrafluoro-1,4,-benzoquinone (p-TFBQ) | light purple | pink-purple | dark purple |
| 2,3,5-trichloro-1,4-benzoquinone | colourless | colourless | pale yellow |
| 2,3-dichloro-5,6-dicyano-1,4-benzoquinone (DDQ) | light orange red | red | red-brown |
| Acenaphthenequinone | colourless | colourless | pale yellow |
| 1-aminoisoquinoline | colourless | colourless | pale yellow |
| hydroquinone | colourless | colourless | pale yellow |
| 2,3-dicyanohydroquinone | colourless | colourless | pale yellow |
| 2,5-dibromo-1,4-benzoquinone | colourless | pale orange | blue-green |
| 2,3,5,6-tetrabromo-1,4-benzoquinone (p-TBBQ) | v. pale yellow | dark green | bright blue |

|  | Propionaldehyde | | |
|---|---|---|---|
| Reagent | Blank | 2CH | 25H-NBOMe |
| 2,3,5,6-tetrachloro-1,4-benzoquinone (p-TCBQ) | colourless | light grey-purple | v. pale green |
| 3,4,5,6-tetrachloro-1,2-benzoquinone (o-TCBQ) | yellow | light orange | pale orange |
| 2,5-Dichloro-1,4-benzoquinone | v. pale pink | pale yellow | v. pale purple |
| 2,6-Dichloro-1,4,-benzoquinone | v. pale yellow-pink | pale yellow | v. pale green |
| Chloranilic acid | light pink-purple | light pink-purple | light pink-purple |
| 2,3,5,6-tetrafluoro-1,4,-benzoquinone (p-TFBQ) | light purple | brown-purple | grey-purple |
| 2,3,5-trichloro-1,4-benzoquinone | colourless | colourless | colourless |
| 2,3-dichloro-5,6-dicyano-1,4-benzoquinone (DDQ) | light orange | brown orange | light orange |
| Acenaphthenequinone | colourless | colourless | colourless |
| 1-aminoisoquinoline | colourless | colourless | colourless |
| hydroquinone | colourless | colourless | colourless |
| 2,3-dicyanohydroquinone | colourless | pale yellow | pale yellow |
| 2,5-dibromo-1,4-benzoquinone | colourless | pale orange | colourless |
| 2,3,5,6-tetrabromo-1,4-benzoquinone (p-TBBQ) | colourless | pale purple | yellow-brown |

|  | Butyraldehyde | | |
|---|---|---|---|
| Reagent | Blank | 2CH | 25H-NBOMe |
| 2,3,5,6-tetrachloro-1,4-benzoquinone (p-TCBQ) | colourless | grey | light b. green |
| 3,4,5,6-tetrachloro-1,2-benzoquinone (o-TCBQ) | yellow | orange | pale orange |
| 2,5-Dichloro-1,4-benzoquinone | v. pale pink | pale yellow | l. brown-purple |
| 2,6-Dichloro-1,4,-benzoquinone | v. pale yellow-pink | pale brown-yellow | pale yellow |
| Chloranilic acid | light pink-purple | light pink-purple | light purple |
| 2,3,5,6-tetrafluoro-1,4,-benzoquinone (p-TFBQ) | light purple | pale purple | pale brown-green |
| 2,3,5-trichloro-1,4-benzoquinone | colourless | colourless | colourless |
| 2,3-dichloro-5,6-dicyano-1,4-benzoquinone (DDQ) | light orange | red-orange | brown orange |

-continued

| | | | |
|---|---|---|---|
| Acenaphthenequinone | colourless | colourless | colourless |
| 1-aminoisoquinoline | colourless | colourless | colourless |
| hydroquinone | colourless | colourless | colourless |
| 2,3-dicyanohydroquinone | colourless | pale yellow | pale yellow |
| 2,5-dibromo-1,4-benzoquinone | colourless | pale orange | colourless |
| 2,3,5,6-tetrabromo-1,4-benzoquinone (p-TBBQ) | colourless | pale purple | brown-green |

| | No aldehyde | | |
|---|---|---|---|
| Reagent | Blank | 2CH | 25H-NBOMe |
| 2,3,5,6-tetrachloro-1,4-benzoquinone (p-TCBQ) | colourless | colourless | colourless |
| 3,4,5,6-tetrachloro-1,2-benzoquinone (o-TCBQ) | yellow | colourless w. orange edge | pale yellow with grey edge |
| 2,5-Dichloro-1,4-benzoquinone | pale red | pale brown | pale green-brown |
| 2,6-Dichloro-1,4,-benzoquinone | pale pink-yellow | v. pale brown | pale brown |
| Chloranilic acid | light pink-purple | light pink-purple | light pink-purple |
| 2,3,5,6-tetrafluoro-1,4-benzoquinone (p-TFBQ) | light purple | light green-yellow | light yellow w. purple edge |
| 2,3,5-trichloro-1,4-benzoquinone | colourless | colourless | colourless |
| 2,3-dichloro-5,6-dicyano-1,4-benzoquinone (DDQ) | light orange | red | dark brown-red |
| Acenaphthenequinone | colourless | colourless | colourless |
| 1-aminoisoquinoline | colourless | colourless | colourless |
| hydroquinone | colourless | colourless | colourless |
| 2,3-dicyanohydroquinone | colourless | pale yellow | pale yellow |
| 2,5-dibromo-1,4-benzoquinone | colourless | pale yellow-orange | colourless |
| 2,3,5,6-tetrabromo-1,4-benzoquinone (p-TBBQ) | colourless | orange | pale yellow |

These results showed that the aldehyde was required, as predicted based on the mechanism put forward, and also that longer chain aldehydes than acetaldehyde do not give the required intense colour changes with specified benzoquinones.

The concentrations of the quinone were also investigated based upon TCBQ. Because the coloured adduct is believed to be very highly coloured, it will be detectable at small concentrations. The sample sizes typically expected for NBOMes are of the order of a few tens of micrograms.

Solutions of TCBQ were prepared over a range of concentrations to assess the effect of the reagent concentration on the resulting colour change. The amount of compound along with the volumes of the test reagents remained constant as the concentration of the TCBQ was varied. It was found that the best concentration was when a TCBQ stock solution of at least $3 \times 10^{-3}$ M was diluted by a factor of about 3, that is a final testing concentration of TCBQ of at least $1 \times 10^{-3}$ M.

Excessively concentrated solutions can present challenges to the naked eye to evaluate, so ideally, the concentration of TCBQ in the test solution is maintained below $3 \times 10^{-2}$ M.

The following initial tests show that the method was reasonably robust as far as the nature of the reagents was concerned, and also appeared to be quite specific as 25H-NBOMe gave a significantly different reaction from the structurally related 2C—H compound.

| | | Colour change | |
|---|---|---|---|
| Test | Reagents used (4 drops of each) | 2C-H | 25H-NBOMe |
| 1 | a) $3 \times 10^{-2}$M TCBQ in 1,4-dioxane<br>b) 8% acetaldehyde in propan-2-ol | Light purple | Light green-blue |
| 2 | a) $3 \times 10^{-3}$M TCBQ in 1,4-dioxane<br>b) Acetaldehyde | Yellow-green | Bright blue |
| 3 | a) $3 \times 10^{-3}$M TCBQ in 1,4-dioxane<br>b) Acetaldehyde<br>c) pH 11.4 phosphate buffer | Yellow-green | Bright blue |
| 4 | a) $3 \times 10^{-3}$M TCBQ in methanol<br>b) Acetaldehyde<br>c) pH 11.4 phosphate buffer | Yellow-green | Light blue |
| 5 | a) $3 \times 10^{-3}$M TCBQ in ethyl acetate<br>b) Acetaldehyde<br>c) pH 11.4 phosphate buffer | Yellow-green | Bright blue |

Although it did not appear to be essential to use a buffer, it is not unusual for NBOMes to be provided in salt form so to ensure these are sufficiently soluble and reactive, a buffer can greatly facilitate the test. To evaluate the best buffer system, the following buffers were prepared:

| pH value | Buffer composition |
|---|---|
| 8.0 | $NaH_2PO_4$ (5.3 mL, 0.2M) & $Na_2HPO_4$ (94.7 mL, 0.2M) |
| 10.9 | $Na_2HPO_4$ (100 mL, 0.05M) & NaOH (6.6 mL, 0.1M) |
| 11.4 | $Na_2HPO_4$ (50 mL, 0.05M) & NaOH (9.1 mL, 0.1M) |
| 12.0 | $Na_2HPO_4$ (100 mL, 0.05M) & NaOH (53.8 mL, 0.1M) |
| 11.0 | $NaHCO_3$ (100 mL, 0.05M) & NaOH (45.4 mL, 0.1M) |

Each of the above buffers was made up to 200 mL with water before a few drops were employed in the standard procedure described above and tested under the same conditions.

There was is little difference between each test and buffer solution in the case of phosphate buffers. The pH 8 and pH 11.4 buffers appear to give a slightly lighter coloured product however the difference was not greatly significant. The pH 12 buffer showed the darkest colour change in comparison although all four buffer solutions could be used to provide a positive result for this test.

The colour change seen with the carbonate buffer was significantly darker than that shown by the phosphate buffer and the differentiation between NBOMes and MDMA and methamphetamine was less than in the case of a phosphate buffer. Although the carbonate buffer was useable, it was preferable to use a phosphate buffer rather than a carbonate buffer.

These results indicate that the method procedure appears robust in terms of the pH value of the buffer solution. While the major component of the buffer remains constant there is little effect on the final colour change result.

The test procedure thus established was carried out on a number of NBOMes. All the NBOMes tested showed a characteristic blue colour either immediately or after 5 minutes. These tests used the preferred combination of neat acetaldehyde, ethyl acetate and buffer. The general recommended procedure is as follows:

To a small (pin head) sized amount of sample in a ceramic spot plate well add:
1) 3 drops pH 11.4 $Na_2HPO_4$—NaOH buffer solution (as described above)
2) 3 drops TCBQ solution
3) 3-4 drops acetaldehyde
4) Observe colour change immediately
5) Observe colour change after 3-5 minutes Tests were conducted on a ceramic spot plate well, but could also be carried out on blotter samples which had been impregnated with NBOMes. The test can also be performed in a tube to minimise evaporation of solvent.

Some agitation of the tube was required but a distinct change was seen within minutes of the addition of reagents. The colour change was bright blue. If necessary, the volume of reagent solution can be increased to ensure a clear colour change can be seen. For instance, an equal amount of each reagent could be used at a volume to the analyst's discretion.

The method is very efficient and no sample preparation or waiting time is required.

In addition to being able to reliably identify the class of substances targeted, a presumptive test should minimise the number of false positives, i.e. should not give positive results on other substances. This is particularly the case in drug tests, where target substances are often adulterated with a variety of household chemicals.

Testing of the specificity of the TCBQ reagent was completed through testing a number of other compounds including other illicit drugs, cutting agents (although in reality, NBOMes rarely contain adulterants or other cutting agents) amines and other white powders which may or may not contain an amine group but would possibly be seen in a seized drug sample.

The results are seen in the following table:

| Compound Class | Compound | Initial Colour change | 5 min colour change |
|---|---|---|---|
| NBOMes | 25H-NBOMe freebase* | blue | NC |
| | 25G-NBOMe HCl | Green-blue | NC |
| | 25D-NBOMe HCl | blue | NC |
| | 25B-NBOMe HCl | blue | NC |
| | 25H-NBOMe HCl | d. blue (slightly) | NC |
| | 25E-NBOMe HCl | blue | NC |
| | 25C-NBOMe HCl | Green-blue | blue |
| | 25I-NBOMe HCl | aqua | blue |
| 2C-X series | 2C-H freebase* | Yellow green | NC |
| | 2C-E HCl | l. yellow-green | brighter green |
| | 2C-D HCl | l. yellow-green | brighter green |
| | 2C-H HCl | l. yellow-green | yellow-green |
| | 2C-T-7 HCl | l. yellow-green | yellow-green |
| | 2C-I HCl | NC | l. yellow-green |
| | 2C-B HCl | l. green | Brighter green |
| Amphetamine type substances | (±)-N-Methyl-3,4-methylenedioxyamphetamine HCl (MDMA) | l. blue | NC |
| | (±)-Methylamphetamine HCl | l. blue | NC |
| | (+)-3-fluoromethamphetamine HCl | v. pale blue | dirty blue-grey |
| | 5-methoxy-N,N-dimethyltryptamine | NC | dirty blue-grey |
| | 2-fluoromethamphetamine HCl | pale blue | NC |
| | 4-methoxymethamphetamine | l. blue | NC |
| | 4-fluoromethamphetamine HCl | l. blue | NC |
| | 2-methylamphetamine (oretamine) HCl | l. yellow-green | NC |
| | (+/−)-3-methylamphetamine HCl | NC | l. yellow-green |
| | (+/−)-3-methylmethamphetamine HCl | pale blue | NC |
| | (+/−)-3-methoxymethamphetamine | pale blue | lighter (colourless) |
| | (+/−)-2-methylmethamphetamine HCl | NC | NC |

| Compound Class | Compound | Initial Colour change | 5 min colour change |
|---|---|---|---|
| | (+/−)-3-methoxyamphetamine HCl | NC | NC |
| | 3-fluoroamphetamine HCl | very pale yellow! | l. yellow-green |
| | 3,4-dimethoxymethamphetamine HCl | very pale blue | l. blue |
| | 4-hydroxyamphetamine | Pale green | l. yellow |
| | 4-methylmethamphetamine HCl | l. blue | l. blue |
| | (+/−)-2-methoxyamphetamine HCl | Pale green | l. green |
| | (+/−)-3,4-dimethoxyamphetamine HCl | l. yellow-green | NC |
| | (+/−)-4-methylthioamphetamine HCl | l. yellow-green | NC |
| | (+/−)-4-bromo-2,5-dimethoxyamphetamine HCl | l. yellow-green | NC |
| | (+/−)-N,N-dimethyl-3,4-methylenedioxyamphetamine HCl | NC | NC |
| | (+/−)-N,N-dimethylamphetamine HCl | NC | NC |
| | (+/−)-N-methyl-1-(3,4-methylenedioxyphenyl)-2-butylamine HCl MBDB | l. blue | NC |
| | 2,5-dimethoxy-4-methylamphetamine HCl | l. green | NC |
| | (+/−)-2-chloroamphetamine HCl | NC | l. green |
| | (+/−)-4-chloroamphetamine HCl | NC | l. green |
| | (+/−)-2-bromoamphetamine HCl | NC | l. green |
| | (+/−)-2-bromomethamphetamine HCl | l. blue | NC |
| | 4-isopropoxy-2,5-dimethoxyphenethylamine HCl | l. yellow | l. yellow-green. Green ring |
| | (+/−)-3-bromomethamphetamine HCl | l. blue | NC |
| | (+/−)-3-bromoamphetamine HCl | NC | pale green |
| | (+/−)-bromo-dragonFLY HCl | pale yellow-green | NC |
| | (+/−)-4-chloro-2,5,-DMA HCl | l. green | brighter green |
| | (+/−)-N-ethyl-3,4-methylenedioxyamphetamine HCl | NC | NC |
| | (+/−)-2,5-dimethoxyamphetamine HCl | l. green | brighter green |
| | (+/−)-3,4,5-trimethoxyamphetamine HCl | l. green | NC |
| | N-ethylamphetamine HCl | very pale blue | NC |
| | (+/−)-4-methoxyamphetamine HCl | l. green | NC |
| | (+/−)-4-methylamphetamine HCl | l. green | brighter green |
| | 3-chloromethamphetamine HCl | l. blue | NC |
| | 4-methoxy-a-pyrrolidinopropiophenone HCl | NC | NC |
| | (+/−)-3-chloroamphetamine HCl | very pale green | NC |
| | (+/−)-4-bromomethamphetamine HCl | l. blue | NC |
| | 2-chloromethamphetamine HCl | l. blue | NC |
| | 4-chloromethamphetamine HCl | l. blue | NC |
| | (+/−)-4-bromoamphetamine HCl | l. green | brighter green |
| Cathinones | (+/−)-a-pyrrolidinopentiophenone HCl | NC | NC |
| | pyrovalerone HCl | NC | NC |
| | (+)-cathinone HCl | NC | NC |
| | 4-hydroxymethcathinone | l. blue | blue |
| | 2-fluoromethcathinone HCl | NC | NC |
| | 3,4-methylenedioxy-N,N-dimethylcathinone HCl | NC | NC |
| | 4-methyl-a-pyrrolidinobutiophenone HCl | NC | NC |
| | iso-ethcathinone HCl | NC | NC |
| | 2,4,5-trimethylmethcathinone HCl | very pale blue | l. blue |
| | 3,4-dimethylnnethcathinone HCl | NC | |
| | (+/−)-N,N-diethylcathinone HCl | NC | possibly l. brown |
| | 4-fluoromethcathinone HCl | NC | NC |
| | (+/−)-N,N-dimethylcathinone HCl | NC | NC |
| | 4-methylethylcathinone HCl | NC | NC |
| | 2,4-dimethylmethcathinone HCl | l. blue | NC |
| | 2,3-dimethylmethcathinone HCl | l. blue | NC |
| | (+/−)-3-bromomethcathinone HCl | pale blue-green | NC |
| | 4-methyl-N-benzylcathinone HCl | l. green-blue | NC |
| | (+/−)-3-fluoromethcathinone HCl | NC | NC |
| | (+/−)-4-fluoroamphetamine HCl | very pale green | NC |
| | 3,4-methylenedioxymethcathinone HCl | NC | NC |
| | (+/−)-4-methylmethcathinone HCl | NC | NC |
| | 4-methylmethcathinone HCl* | Pale yellow | v. pale aqua |
| | 2-fluoroamphetamine HCl | l. yellow | NC |
| | butylone HCl | green-blue ring | NC |
| | 3,4-methylenedioxypyrovalerone HCl | NC | NC |
| | 3,4-methylenedioxypyrovalerone HCl* | NC | NC |

-continued

| Compound Class | Compound | Initial Colour change | 5 min colour change |
|---|---|---|---|
| | 4-methoxymethcathinone HCl | NC | NC |
| | 3-methylmethcathinone HCl | NC | NC |
| | 2-methylmethcathinone HCl | light green-blue ring | NC |
| | 4-bromomethcathinone HCl | green-blue ring | NC |
| Piperazines | 1-(4-chlorophenyl)-piperazine · 2HCl | l. blue | NC |
| | methylbenzylpiperazine · 2HCl | NC | NC |
| | 1-(4-fluorophenyl)-piperazine · 2HCl | pale blue | NC |
| Tryptamines | 5-methoxy-N,N-dimethyltryptamine | NC | dirty blue-grey |
| | 5-methoxy-N,N-diallyltryptamine | pale purple | NC |
| Other precursors and illicit substances | Methylamine HCl | Pale green | Light green |
| | Pseudoephedrine | Pale green | Green-blue |
| | Ephedrine | Very pale blue | l. green-blue |
| Common cutting agents | Lidocaine | Pale green | NC |
| | Paracetamol | Pale yellow | v. pale peach |
| | Ibuprofen | NC | Pale yellow |
| | Caffeine | Pale yellow | Pale yellow |
| | Tetramisole HCl | Pale yellow | v. pale orange |
| | 4-Methoxy phenol (MEHQ) | Pale purple | Darker purple |
| | 3,4-dimethoxyphenethylamine | Brown | NC |
| | Magnesium stearate | Pale yellow | Pale yellow |
| | Benzocaine | NC | v. pale purple |
| | Phenobarbital | Brown-yellow | Purple |
| | Salicylamide | Pale yellow | NC |
| | Aspirin | Pale yellow | NC |
| | Creatine | Pale peach | NC |
| | 4-aminophenazone | Brown-purple | Orange-brown |
| | Quinine | Pale yellow | Pale grey-brown |
| | Dimethyl sulfone | NC | NC |
| | Thiaminium dichloride | NC | NC |
| | Inositol | NC | NC |
| | L-ascorbic acid | NC | NC |
| | Mannitol | NC | NC |
| | Benzoic acid | NC | NC |
| | Citric acid | NC | NC |
| | Phenolphthalein | NC | NC |
| | Sorbitol | NC | NC |
| | Phenacetin | NC | NC |
| Sugars | Lactose | NC | NC |
| | d-glucose | NC | NC |
| | Sucrose | NC | NC |
| | D(−)-fructose | NC | NC |
| | Cellulose | Pale yellow | NC |
| Amines and amino acids | Aniline | Dark brown | NC |
| | Glycine | Pale yellow | Brighter yellow |
| | Ethylenediamine-N-N'-diacetic acid | NC | Pale orange |
| | diphenylamine | Pale purple-blue | Blue ring |
| | Phenylalanine | NC | NC |
| | L-valine | NC | NC |
| | L-phenyldiamine | NC | NC |
| | L-threonine | NC | NC |
| | D-alanine | NC | NC |
| | Ethylenediamine | NC | NC |
| | Methoxylamine HCl | NC | NC |

In total, 100 illicit substances and precursor chemicals were tested with the developed TCBQ method. Another 41 common cutting agents, sugars, amines and amino acids were also tested to assess the selectivity of the method. Seven 25-NBOMe analogues along with the synthesised 25H-NBOMe freebase were tested to assess the specificity of the developed method.

An ideal result would see all 25-NBOMe analogues resulting in the same or highly similar colour change with the reagent solution and no, or few other compounds reacting in the same way. The reagent used in this study is in itself not highly selective toward 25-NBOMe compounds as it appears to target the amine functional group. This would assume that all compounds containing a primary or secondary amine would react with this reagent in some way. The table above illustrates however, that few compounds, even those containing amine functional groups react with TCBQ to afford the same bright blue colour change as the 25-NBOMe compounds.

The seven tested 25-NBOMe analogues all resulted in the bright blue colour attributed to a positive test result. 25G, 25C and 25I-NBOMe took several minutes to afford this colour and the initial colour change was to a lighter green-blue or aqua colour. Some other secondary amine containing substances showed a light blue colour which was readily distinguishable from the brighter blue produced by the 25-NBOMe analogues. This colour appears to be relatively consistent with the presence of a secondary amine like that in methamphetamine and its derivatives.

Generally this colour change was not seen with the cathinone analogues or the piperazines however there were several exceptions. 2,4-dimethylmethcathinone, 2,3-dimethylmethcathinone, 1-(4-chlorophenyl)-piperazine-2HCl and 1-(4-fluorophenyl)-piperazine-2HCl resulted in light or pale blue colour changes with the TCBQ. These resulting colours were similar to that seen of methamphetamine and MDMA and can still be readily distinguished from the 25-NBOMe analogues.

4-Hydroxymethcathinone initially showed a light blue colour however, the result darkened after several minutes to afford a colour similar to that produced by the 25-NBOMe analogues. This was the only significant false positive. This was not seen as particularly problematic, as 4-hydroxymethcathinone is still an illicit substance.

It is clear that a large amount of methamphetamine or MDMA would be required to develop a positive test result similar to that seen with even a small amount of NBOMe. Thus, MDMA or methamphetamine are unlikely to give the requisite colour intensity for a positive presumptive test. Comparative Limit of Detection studies are detailed below.

The 2C series compounds resulted in a bright yellow green colour change and similarly many of the amphetamine derivatives also resulted in a yellow or green colour. This colour change would appear to be due to the reaction with the primary amine of which these compounds possess. This colour change did not appear to be specific for any particular group of compounds but may be used as an indication of the type of substance which is being tested even if the result is not 'positive'.

All the NBOMes had a characteristic strong blue colour, with the exception of 25G-NBOMe which was green blue. The blue colour was presumptive for NBOMes. Of the other agents tested, only a small number gave a result that could be considered even close to the NBOMe result and even then, the intensity is unlikely to be interpreted as a false result. Less than 2% of compounds tested gave a false positive result.

The assessment of the repeatability showed that with the same reagent this method will produce the same colour change for 25H-NBOMe over multiple tests. No significant changes were seen across different spot plates. Tests completed using the micro-well plates appeared to give a darker blue colour change, but this could be ascribed to the increased concentration of the sample and reagents in a small yet deeper well in comparison to the flat wells of the spot plates.

The colour persisted for a sufficient time to be of value for a presumptive test. These results indicate that this test has a high level of both repeatability and reproducibility. The stability of the coloured product generated from a test for 25H-NBOMe using p-TCBQ ($3 \times 10^{-3}$ M) in ethyl acetate, acetaldehyde and $PO_4$ buffer solution was monitored and is shown in the following table.

| Time elapsed | Colour with 25H-NBOMe |
| --- | --- |
| 0 minutes | Bright blue |
| 20 minutes | Bright blue |
| 40 minutes | Bright blue |
| 1 hour | Bright blue |
| 2 hours | Bright blue (slightly darker) |
| 20 hours | Dark blue |
| 24 hours | Dark blue |
| 44 hours | Black-blue |
| 48 hours | Black-blue |

The colour was thus seen to remain unchanged for several hours at least, but darkened over 1-2 days Another important factor for presumptive testing, alongside selectivity, is sensitivity. The limit of detection (LOD) was determined using a modified version of the method outlined by the National Institute of Justice's Colour Test Standard. Twelve different volumes of a 25H-NBOMe methanolic solution (1×10-3 M) were added to a micro well plate ranging from 0-500 μL. This was completed in replicate of four in the same well plate. The methanol was evaporated before general testing procedures were applied and colour change observed. The point at which the colour was not a significant change from the reagent blank was considered to be the LOD of the compound however the operational LOD would be 10 times this value.

The blue colour change could be seen at very low volumes of 25H-NBOMe. A change which may no longer be confirmed as positive was where the amount of 25H-NBOMe present was 22.5 μg (225 μg operational), an amount much smaller than that commonly seen on a single blotter paper (250-500 μg). Thus, the present test is likely to be of sufficient sensitivity to detect any quantity of NBOMe being sold or used.

A comparative LOD study was also conducted including methamphetamine, MDMA and pseudoephedrine alongside the 25H-NBOMe. The pseudoephedrine did not produce a colour change. Both methamphetamine and MDMA even at very high concentrations showed colour change comparable with the point at which 25H-NBOMe would no longer give a clear positive result. This result is ideal when one considers that in reality, the amount of methamphetamine or MDMA in a sample is unlikely ever to be high enough to trigger a presumptive positive result for NBOMes.

The ability of test reagents to be stored was also investigated. Each solvent solution showed differing results between the stored reagent solutions. The physical appearance of the solutions did not immediately indicate that degradation had occurred.

Several different reagent solutions, including both the TCBQ and the buffer solution were used over several days and in different combinations. These changes did not affect the colour change result of the testing with 25H-NBOMe. The resulting colour changes from tests performed on different days of testing showed no significant differences. Certain test days showed some evaporation of the reagent solutions and a concentrated colour ring around the edge of the spot plate rather than a consistent colour throughout the well but this appeared to be the result of environmental factors. In any event, the colour change of these tests did not appear to be affected by these factors and a clear colour change could be readily identified. Tests conducted on reference materials different laboratories displayed little difference in the colour change presented by these compounds.

The stability of 1,4-dioxane and ethyl acetate solutions were compared. The 1,4-dioxane solutions stored in a refrigerator for four weeks away from light showed results not that dissimilar from a positive test using fresh solutions, although the colour was somewhat lighter. 1,4, dioxane solutions stored on the bench showed that degradation of the test solution had occurred.

As mentioned above, NBOMes are often supplied as impregnated materials on blotters. It was found that advantageously, the present method can be directly applied to blotter paper samples, a common dosage form of 25-NBOMe administration, without the need for an extraction procedure.

Two blotter paper tabs (perforated squares) applied with 25B-NBOMe were prepared for comparative analysis. The 25B-NBOMe was applied using a solution of acetonitrile containing 500 μg of compound and allowing the solvent to evaporate so that each tab contained approximately 250 µg. One tab was placed in 500 µL of analytical grade methanol and soaked for 1 h after which the tab was removed and the methanol was evaporated. To this tube and another tube containing the other blotter paper, 5 drops of each the pH 11.4 buffer, TCBQ in ethyl acetate and acetaldehyde was added and colour change observed.

The TCBQ showed quality results with a bright blue colour change in the presence of the 25-NBOMe compounds. The analysis of the compound on the blotter paper was successful with no extraction method required to obtain a positive result. The use of ethyl acetate as the reagent solvent is the preferred method as it allows for a safer practice when used in comparison to the 1,4-dioxane and it still provides satisfactory results.

The method of the present invention are useful visual tests because of the colour change. However, the test lends itself to being conducted in a more automated or standardised manner if desired.

A device suitable for detection of the colour change is shown in FIG. 1A. A collection swab has an absorbent end section 10 which can be used to collect particles of the suspected drug material for collection. The absorbent portion is mounted on an elongate shaft 11 which connects to the inside of a cuvette lid 12. In use, the absorbent end of the swab is inserted into the cuvette 13 and the cuvette lid is sealingly engaged with the cuvette. The cuvette contains the necessary reagents 14 to detect an NBOMe. Upon sealing engagement, the absorbent portion contacts the reagents and the colour change to bright blue indicative of an NBOMe develops. The cuvette as exemplified is of square cross section and has equal optical paths in the x-y plane. This would render the cuvette suitable for both naked eye and instrument detection In FIG. 1B, the cuvette 13 can also have an adjacent reference cuvette 15 integrally formed therewith, which would show the background solution colour and make the colour change more obvious.

In FIG. 1C, the cuvette 13 can also have another chamber 16 attached in proximity thereto which contains no reagents to allow for simultaneous collection and retention of a portion of the sample for further analysis in the event that the validity of the presumptive test is challenged.

A particular embodiment of the test kit is shown in FIG. 2. A collection swab 20 has an absorbent end section 10 which can be used to collect particles of the suspected drug material for collection. The absorbent portion 10 is mounted on an elongate shaft 11 which connects to the inside of a tube lid 21. In use, the absorbent end of the swab is inserted into the tube 22 and the tube lid 21 is sealingly engaged with the tube, e.g. by means of interlocking threads 23. The tube 22 contains the necessary reagents 14 and a dense organic layer 24. Upon sealing engagement, the absorbent portion 10 contacts the aqueous reagents 14 and the complexation begins, thereby developing the necessary colour. An optional heavy organic layer 24 (e.g. chloroform or dichloromethane) may be provided to extract the and intensify the coloured adduct away from impurities. The tube desirably has a reduced cross section at the lower portion to enable better examination of a small amount of solvent.

The lower tip shown in FIG. 2 is conical, although this is not a necessary condition and in many cases it is preferred that the reduced path has a lower portion of reduced cross section with a constant profile. A lower portion of reduced but constant square cross section for example may be more amenable for use in instrumental analysis.

It was noted that the order of addition of NBOMe sample, TCBQ, aldehyde or solvent had no effect upon the final colour produced by the test. The relative amounts of the compounds were also found, within reason, not to impact on the outcome of the test. It is important to bear in mind that in the field, the amount of seized material tested, and the relative amount of NBOMe contained therein will not be known with any precision. Field tests need to be quite robust and relatively insensitive to the exact amount of drug. The methods of the present invention are suitably robust and in general, the tests can be carried out using rough or approximate quantities of drug and reagent without obtaining a materially different test outcome.

The amount of the drug used or contained within the sample does however affect the time for the colour change to occur and the depth of colour. However, it is usual for NBOMes to be supplied on a blotter and typical amounts are well in excess of the LOD of the present method.

A potential drawback of any test that relies upon inspection by the naked eye is that there can be numerous factors impacting upon what would be considered to constitute a determinative colour change. This can be particularly challenging in the case of field tests for drugs where the lighting conditions and stresses on the analyst would generally be much less favourable than those in the laboratory. Instrumental analysis can help overcome this potential problem.

Non-limiting examples of some colorimetric analysis devices envisaged to be suitable for carrying out the tests of the present invention are shown in FIG. 3. In all the embodiments shown, the device 50 has a cavity designed to hold a sample tube 22 and an inspection window or windows configured to allow spectroscopic analysis of a relevant coloured section of the material contained in the tube. The cavity is configured so as to generally occlude the rest of the tube apart from the inspection window or windows. This functions so as to provide controlled light conditions inside the device.

Figure 3A:
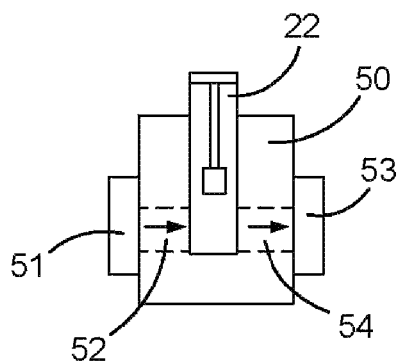
FIGS. 3a-f shows a variety of exemplary configurations of devices of the present invention.
Figure 3B:
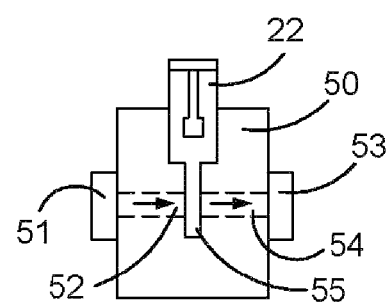
Figure 3C:
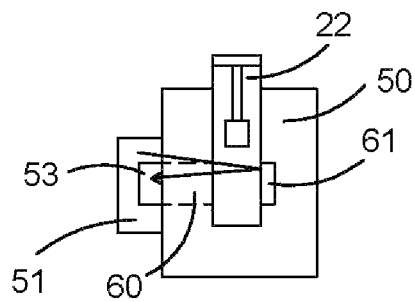
Figure 3D:
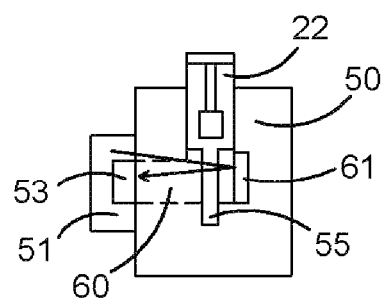
Figure 3E:
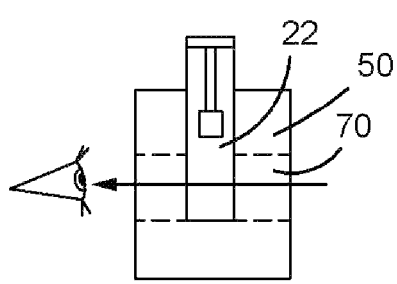
Figure 3F:
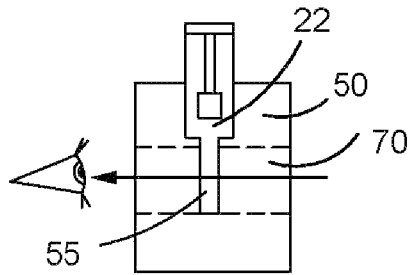

The specific device in 3a and 3b has two opposed windows to allow a light from a light source 51 to enter from a first window 52 and exit to a detector 53 at an opposed window 54. The detector could be any sort of visible detector, or even a simple RGB detector. In FIG. 3a, the tube 22 is of continuous cross section, whereas in 3b, it is of reduced cross section 55 at its lower end to accommodate the heavy organic phase with increased concentration of the coloured complex.

Alternatively, the device as shown in 3c and 3d could have a single window 60 with an opposed reflective portion 62, where the light enters and exits via the same window 60, after passing twice through the sample, before entering detector 53. 3d also has a region of reduced cross section 55.

Alternatively, the device as shown in 3e and 3f could be configured for hand held use. The device has a through passage 70 to enable visual inspection of the tube 22 (or reduced portion 55) without interference. Light passing through the sample is simply observed with the naked eye. This embodiment could advantageously contain a reference sample for side-by side comparison.

Colorimetric devices according to the present invention can be made in portable or mobile form, and the accompanying software can be configured to analyse the output of the RGB or other detector and provide simply a positive or negative result for the presence of an NBOMe.

It was also found possible to prepare the reagents in the form of a single part solution. The three reagents were combined into one solution. This test solution was used on several drug samples and afforded results identical to those from adding the reagents sequentially.

This single-part test solution was found to remain effective weeks after preparation in the case of ethyl acetate solvent. The use of a single-part solution will make the test method significantly simpler to use in the field.

Figures 4A, 4B, 4C:
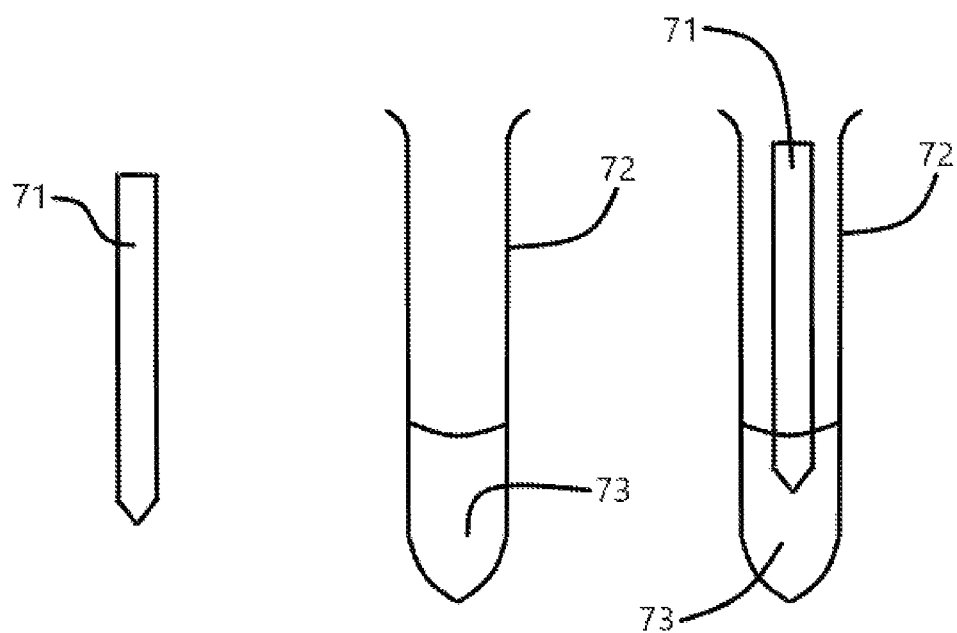
FIGS. 4a-c shows a test in a paper-based format.

This test can also be used in a paper-based format as shown in FIG. 4. The quinone reagent can be applied to a filter paper strip 71 which may have wax printed channels. This can be done by soaking the paper in the reagent solution or applying the required amount dropwise. The drug is added to and dissolved in the buffer and aldehyde solution 73 in sample tube 72 before addition of the paper strip. The colour change then occurs once the drug and other two reagents react on the paper.

Once the quinone reagent has been added to the paper, this paper can be stored in a closed vial and remain effective for weeks after preparation. After addition of the reagent to the paper, the paper can be used immediately while still wet or after the solvent has evaporated and will afford the same blue colour change result.

Similar results are also seen if the drug solution is added to the paper first and is then added to a vial containing all three reagents.

The invention claimed is:

1. A method of detecting the presence of an NBOMe in a sample, the method comprising the steps of contacting the sample with an activated p-quinone, and an aldehyde and observing a colour change, which when present, correlates with the presence of an NBOMe.

2. A method according to claim 1 wherein the activated p-quinone is substituted with one or more leaving groups.

3. A method according to claim 2 wherein the one or more leaving groups are independently selected from chlorine or bromine.

4. A method according to claim 1 wherein the activated p-quinone is symmetrical and is selected from a di- or tetra-substituted p-quinone.

5. A method according to claim 3 wherein the activated p-quinone is symmetrical and is selected from 2,3,5,6-tetrachloro-1,4-benzoquinone, 2,3-dibromo-1,4-benzoquinone, 2,3-dichloro-1,4-benzoquinone, 1,6-dibromo-1,4-benzoquinone, 1,6-dichloro-1,4-benzoquinone, 2,5-dibromo or 2,5-dichloro-1,4-benzoquinone.

6. A method according to claim 4 wherein the active p-quinone is 2,3,5,6-tetrachloro-1,4-benzoquinone (TCBQ).

7. A method according to claim 1 wherein the aldehyde is acetaldehyde.

8. A method according claim 1 wherein the activated p-quinone is provided in a solvent selected from ethyl acetate, methanol or 1,4-dioxane.

9. The method according to claim 1 further including a buffer to maintain an alkaline environment.

10. The method according to claim 1 wherein the aldehyde and the active p-quinone are present in equimolar amounts.

11. The method according to claim 1 wherein a colour change is observed at environmental temperature within 5 minutes.

12. The method according to claim 1 wherein the order of addition to the sample is: 1) buffer
2) a solution of TCBQ and acetaldehyde.

13. The method according to claim 1 wherein the buffer, TCBQ and acetaldehyde are contacted simultaneously with the sample.

14. The method according to claim 1 wherein the acetaldehyde is contacted with the sample prior to the addition of TCBQ.

15. A method according to claim 1 which takes place on a plate or well to allow visualisation of developed colour, where present.

16. A method according to claim 1 which takes place on a paper substrate.

17. A test reagent for detecting the presence of an NBOMe in a sample, the reagent comprising TCBQ and acetaldehyde and a solvent.

18. A test reagent according to claim 17 further comprising a solvent selected from 1,4-dioxane and ethyl acetate.

19. A kit for the detection of an NBOMe cathinone moiety, the kit comprising the test reagent of claim 17.

20. A kit according to claim 19 further comprising a colour standard or comparison chart.

* * * * *